United States Patent [19]

Gefter

[11] Patent Number: 4,459,361

[45] Date of Patent: Jul. 10, 1984

[54] LIGAND ASSAY WITH ONE OR TWO PARTICULATE REAGENTS AND FILTER

[75] Inventor: Malcolm L. Gefter, Newton, Mass.

[73] Assignee: Angenics, Inc., Cambridge, Mass.

[21] Appl. No.: 385,052

[22] Filed: Jun. 4, 1982

[51] Int. Cl.³ ............................................. G01N 33/54
[52] U.S. Cl. .................................... 436/523; 210/650; 210/654; 422/61; 436/532; 436/533; 436/534; 436/541; 436/808; 436/824
[58] Field of Search ............... 436/533, 534, 541, 523, 436/824, 532, 808; 210/650, 654; 422/61

[56] References Cited

U.S. PATENT DOCUMENTS

| | | |
|---|---|---|
| Re. 29,474 | 11/1977 | Axen et al. . |
| 3,442,819 | 5/1969 | Herbert ................................ 436/541 |
| 3,492,396 | 1/1970 | Dalton .............................. 436/541 X |
| 3,862,303 | 1/1975 | Anderson . |
| 4,062,935 | 12/1977 | Masson et al. . |
| 4,091,089 | 5/1978 | Chichibu et al. . |
| 4,115,535 | 9/1978 | Giaever . |
| 4,138,213 | 2/1979 | Masson et al. . |
| 4,143,124 | 3/1979 | Masson et al. . |
| 4,184,849 | 1/1980 | Cambiaso ............................ 436/523 |
| 4,191,739 | 3/1980 | Uzgiris et al. . |
| 4,202,872 | 5/1980 | Collen . |
| 4,210,723 | 7/1980 | Dorman .......................... 436/534 X |
| 4,235,960 | 11/1980 | Sasse et al. . |
| 4,256,724 | 3/1981 | Rutner et al. . |
| 4,279,617 | 7/1981 | Masson . |
| 4,305,925 | 12/1981 | Kapmeyer ...................... 436/523 X |
| 4,308,026 | 12/1981 | Mochida . |
| 4,308,145 | 12/1981 | Higley ............................. 210/654 X |

OTHER PUBLICATIONS

Engvall, *Methods in Enzymology*, 70:419-39, (1980).
Von Schulthess et al., *Molecular Immunology*, 17:81-92, (1980).
Masson, et al., *Methods in Enzymology*, 74:106, (1981).
Cohen, et al., *Immunochemistry*, 12:349, (1975).
Blume, et al., *Clinical Chemistry*, 21:1234, (1975).
Hoigne, et al., *Acta Allergologia*, 13:364, (1959).
Grange, et al., *J. Imm. Methods*, 18:365-375, (1977).
Kohler, et al., *Nature*, 256:495, (1975).
Kohler, et al., *Eur. J. Immunol.*, 16:511, (1976).
Thorell et al., "Radioimmunoassay and Related Techniques", pp. 3-10, C. V. Mosby, Saint Louis, 1978.

*Primary Examiner*—Sidney Marantz
*Attorney, Agent, or Firm*—David G. Conlin

[57] ABSTRACT

Method of making and using products for analysis of specific ligands in solution. More specifically, a method of analyzing a sample for a ligand by incubating the sample with a ligand selective binder and with a predetermined amount of ligand, the binder and/or the predetermined amount of ligand being borne by particles of predetermined size, filtering the solution and analyzing the particles which pass through the filter and/or those particles that do not pass through the filter.

23 Claims, 2 Drawing Figures

LIGAND ASSAY WITH ONE OR TWO PARTICULATE REAGENTS AND FILTER

This invention relates to methods and products for analyzing materials and detecting specific compounds in mixtures of what may be chemically similar compounds. More particularly, this invention relates to methods and products for analysis of specific ligands or other compounds by a ligand assay which is much simpler, less expensive, as specific and often more accurate than the cumbersome radioimmunoassay, enzyme-immunoassay or other assay techniques previously known.

Progress in the study of biochemistry has been advanced considerably by the discovery of radioimmunoassay techniques, which permit analysis for specific proteins and other ligands in a melange of biologic materials, and determination of the concentration of that substance with very high accuracy. See Thorell et al., *Radioimmunossay and Related Techniques* (C. V. Mosby, 1978), the disclosure of which is incorporated herein by reference.

The typical radioimmunoassay (RIA) techniques depend on competitive binding of the compound to be measured (ligand) and radiolabelled ligand with an antibody or other receptor which specifically binds that ligand. Thus, for example, radioimmunoassay analysis for a particular ligand usually initially involves radiolabelling a sample of that compound, and obtaining an antibody or other binder which specifically binds to that compound. The antibody is usually obtained by injecting the ligand as an immunogen into an animal such as a rabbit, and utilizing the antisera produced by the animal.

Having these basic reagents, samples containing unknown amounts of the ligand can be analyzed by mixing the sample, the radiolabelled ligand, and the ligand binder together, preferably for a period of time sufficient to permit equilibrium to be attained in the reaction between the radiolabelled ligand, the ligand (if any) in the sample to be analyzed, and the binder for ligand The ligand binder, and its bound (labelled and unlabelled) ligand are then separated from the unbound (labell and unlabelled) ligand, e.g., by precipitation of the binder, and the radioactivity of the bound material is counted by a radiation detecting apparatus. The higher the level of (unlabelled) ligand in the sample to be analyzed, the more of that unlabelled ligand will be bound to the binder. Thus the unknown concentration of the ligand in the sample to be analyzed varies inversely with the radioactivity detected in the bound fraction.

While these techniques have been substantial improvements over previously available methods, they are extremely cumbersome, requiring radioactive reactants and typically large, expensive radioactivity counting devices, and large amounts of time to get the samples collected, counted and to interpret the results. Further, the use of radioactivity requires a balance between the desired sensitivity and the functionality of the compounds to be detected. For example, in order to obtain the maximum sensitivity, the radioactivity may be increased, so that even small amounts of bound radioactive materials can be detected. However, high radioactivity tends to degrade the reactants and interfere with the chemistry involved. Further, radioactive reagents, in addition to posing radiation hazards, break down and thus do not have great stability.

The cumbersomeness of RIA techniques have in part led to other immunoassay techniques, such as the enzymatic approaches, wherein the ligand is bound to an enzyme. See, e.g., Engvall, "Enzyme Immunoassay ELISA and EMIT," 70 *Methods in Enzymology* 419 (1980), which is hereby incorporated by reference. For example, an enzyme-bound ligand may be mixed with an unknown amount of unbound ligand from the sample to be analyzed. The ligand which is bound to the enzyme is analyzed by contact with reactants, and observing a reaction, or measuring the rate of a reaction, which is catalyzed by that enzyme. As in RIA, the higher the amount of bound ligand after incubation, the lower the concentration of the unbound ligand in the sample.

Other variations are described by Engvall, supra. As also pointed out, enzyme-immunoassay techniques are limited in this application, and suffer from a number of serious disadvantages. These include the necessity of having large amounts of pure antigen or antibody in order to effectively label with enzymes; the adverse effects on the enzymes caused by competitive enzymes and/or inhibitors in common biological sample fluids such as serum, urine, etc.; difficulties in identifying enzymes which are readily detectable at nanogram levels and have the requisite availability, cost and shelf life; etc. See Engvall, supra, 70 *Immunochemical Techniques* at 423–425.

Other techniques which have been developed include agglutination techniques, where a specific reagent, such as an antibody, is bound to inert particles and mixed with one or more dilutions of samples to be tested. The coated particles are crosslinked or otherwise aggregated by a complementary antibody or multivalent antigen. See, e.g., Von Schulthess et al, "*Detection of Agglutination Reactions Using Anistropic Light Scattering * * *,*" 17 Molecular Immunology, 81–92 (1980), the disclosure of which is hereby incorporated by reference. However those methods involve specialized light scattering devices or other devices necessary for use of turbidimetric techniques to measure the number of agglutinated particles. Von Schulthess et al, supra; Masson et al, "Particle Counting Immunoassay," 74 *Methods in Enzymology* 106 (1981), the disclosure of which is hereby incorporated by reference; Cohen et al, "Immunoassay by Light Scattering Spectroscopy," 12 *Immunochemistry* 349 (1975), the disclosure of which is hereby incorporated by reference; Blume et al, "Application of Differential Light Scattering to the Latex Agglutination Assay for Rheumatoid Factor," 21 *Clin. Chem.* 1234 (1925), the disclosure of which is hereby incorporated by reference; Hoigne et al, "Serologic Studies on Serum of Drug Allergies with a Polystyrene-Latex Technique Measured by Nephelometry," 13 *Acta Allergologia* 364 (1959), the disclosure of which is hereby incorporated by reference; and Grange et al, "Nephelometric Assay of Antigens and Antibodies with Latex Particles," 18 *J. Imm. Methods* 365-375 (1977), the disclosure of which is hereby incorporated by reference.

It is accordingly an object of the present invention to provide a method of analysis which is as sensitive as, or preferably more sensitive than, previous immunoassay techniques, but without requiring tagging of ligands or antibodies with radioactive materials, enzymes, fluorochromes or other tags.

It is a further object of the invention to provide a method of analysis which is at least as sensitive as prior immunoassay techniques, but does not require the complex, time consuming manipulative steps of previous immunoassay techniques.

It is a further object of the invention to provide a method of analysis which is at least as sensitive as radioimmunoassay techniques, but which does not require the expensive and complicated apparatus which is required to utilize radioimmunoassay techniques.

It is a further object of the invention to provide immunoassay reactants and products which can be used to analyze accurately for minute quantities of ligand by persons with little or no technical training.

It is a further object of the present invention to provide methods and products for particulate immunoassay which do not require sophisticated particle analyzers or other complicated apparatus in order to obtain accurate analyses.

These and other objects and advantages, which will be apparent to the skilled in the art from the present disclosure or practice of the invention as disclosed herein, are achieved by use of the methods and products described more particularly below.

DESCRIPTION OF THE PREFERRED EMBODIMENTS

Figure 1:
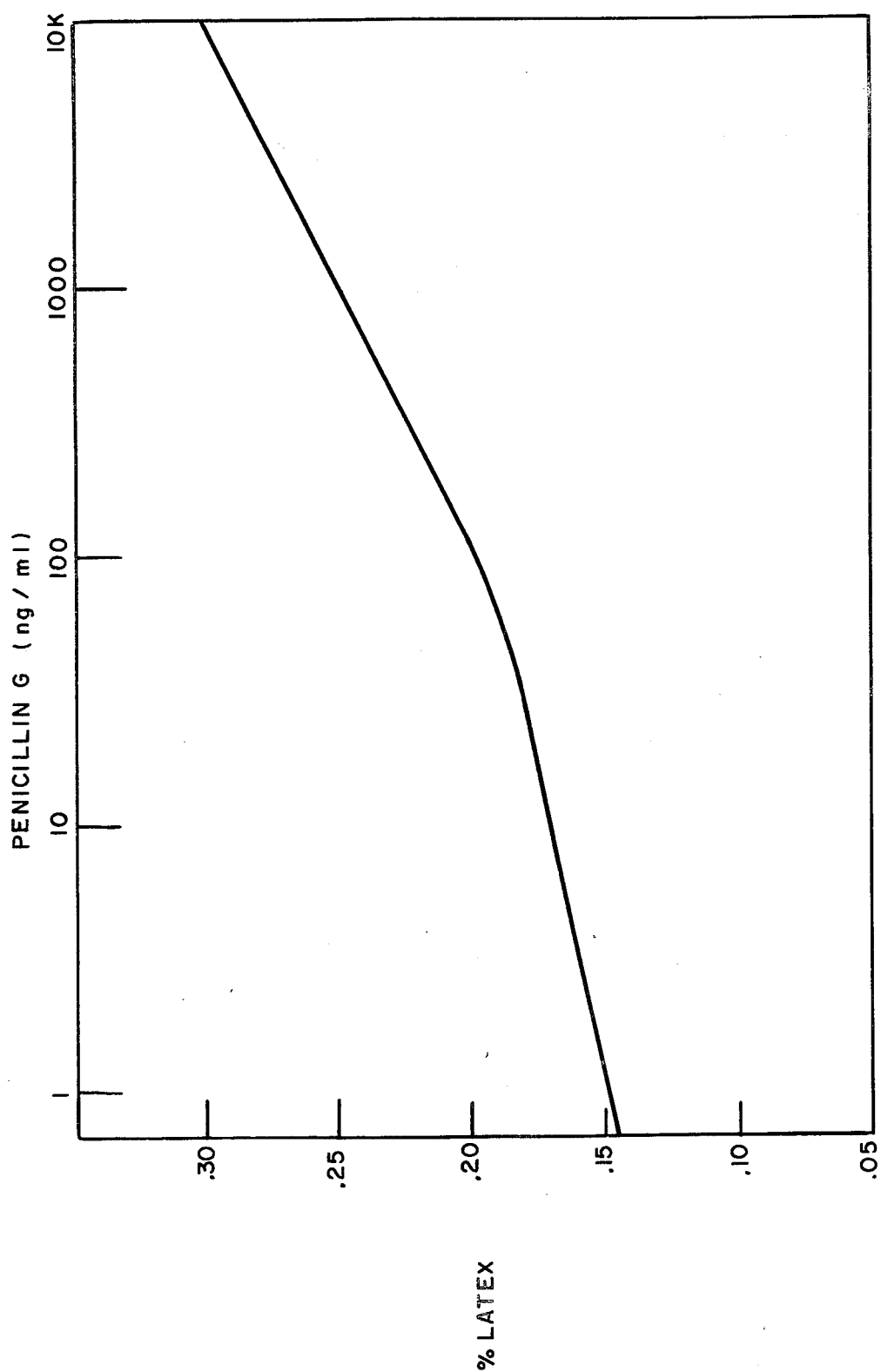
FIG. 1 is a graphical representation of a standard curve obtained by utilizing the present invention in connection with analysis of various concentrations of penicillin G in a phosphate buffer.

Prior particulate immunoassay techniques have not solved the problems which have prevented the utilization of immunoassay techniques by anyone not having access to complex, sensitive equipment, such as the blood cell counter of Masson et al, the photocolorimeter/nephelometer of Hoigne et al, the spectrophotometer, Photogoniodiffusometer, differential spectrofluorimeter and particle counter of Grange et al, supra, etc. This fact sharply restricts the use of particle immunoassay techniques, and prevents their use in many areas where they could be most useful.

For example, one problem which has occurred is the ingestion by humans of antibiotics contained in milk. Dairy farmers use antibiotics, typically B-lactam antibiotics such as derivatives of penicillins and cephalosporins, to treat a variety of disorders, such as mastitis, in their cows. When those antibiotics show up in the milk, ingestion by humans can lead to reduced effectiveness of those antibiotics in treating human disorders, and sometimes can precipitate allergic reactions. In addition, antibiotics in milk inhibit the production of biologically derived milk products such as cheese, yogurt, etc.

Accordingly, the FDA has set stringent standards for level of antibiotics which can be contained in milk. As a practical matter, if milk contains more than 0.01 Internationl Unit of B-lactam antibiotic per ml (equal to about 6 ng/ml for penicillin G), it is unacceptable and cannot be sold for human consumption.

Typically, at present, milk collected by tank trucks from different farms is tested for antibiotic content at the processing center. This testing, using RIA or similarly cumbersome techniques or even slower microbiological inhibition techniques, should be performed before the truck is unloaded, to prevent contamination of large volumes of previously unloaded milk. The loss of time is a large financial burden on the trucker, and rejection of the whole truck load of milk is an even larger burden on the farmers whose milk filled the truck and on the milk cooperative or dairy. If the contaminated milk, perhaps from one herd or even from one cow, could be detected and prevented from being loaded into the tank truck, this substantial loss could be prevented. However, the truck driver or the farmer can hardly be expected to carry with him or operate a chemical laboratory, including scintillation or radiation counters for RIA analysis, or the sensitive blood cell counters, etc. required for previous particulate techniques.

The present invention is ideal for this and other similar situations. The present invention provides a simple, rapid, accurate test, which can be used in minutes by the milk collection center to let the trucker rapidly unload and get back to work without waiting hours for test results. It provides a simple, rapid, accurate test which is so straightforward that truckers and farmers can easily utilize it to prevent contaminated milk from being collected, or to determine when a cow which has been treated with antibiotics can be put back into production. Other similarly advantageous uses will be readily apparent to the skilled in the art.

In accordance with one preferred embodiment of the present invention, a ligand-binding protein or other material (binder) is immobilized on a particle of defined dimensions, preferably a plastic particle having a spherical shape and defined uniform diameter. The binder can be an antibody, an enzyme, or any protein or other material which specifically binds to the ligand and of interest. A known amount of the ligand and to be determined is preferably also immobilized which may be on a similar particle. The amounts of immobilized binder, immobilized ligand and, and particles are preferably adjusted so that, in the absence of some type of binding inhibition, each of the binder-bearing particles will aggregate with one or more of the ligand-bearing particles, when mixed together for a reasonable time (incubated).

During the test the particles after mixing are exposed to a filter having a defined pore size which is larger than, but close to, the coated particle size, so that aggregated particles will normally not pass through the filter. For example, where the particles have a diameter of 0.3 $\mu$m, a filter having a pore size of 0.4 $\mu$m might be used.

Where the proportions of materials are adjusted so that essentially all of the coated particles will aggregate upon mixing, the presence of ligand in a sample to be tested can be determined by admixing the sample with the binder-bearing particles, prior to or at the same time those particles are mixed with the ligand-bearing particles. The ligand (if any) in that sample competes for binding sites on the binder-bearing particles with the ligand immobilizer or the ligand-bearing particles. Where the ligand from the sample is bound to the binding sites on the binder-bearing particles, the ligand-bearing particles are prevented from aggregating with the binder particles. Thus when the mixture of particles is thereafter subjected to filtration through the filter having a controlled pore size, there is a very substantial increase in the amount of unaggregated particles which pass through the filter. The number of such unaggregated particles can be sufficient to be visible to the naked eye, and this visiblity can also be enhanced, e.g., by selection of the size, color, optical density, fluorescence or other properties of the particles. For example, the particles can also have enzymes attached to the partical surface, and which enzymes can catalyze a color change on a substrate, thus making the results highly visible in another way.

Thus the lab technician, farmer, truck driver, etc. can see after only a short mixing period whether there is ligand in the sample, without having to wait to run the sample through a radiation counter, spectrophotometer, fluorometer, goniodiffusimeter, etc. to get the results.

In a further preferred embodiment, one of the particles is larger than the other, and in fact is too large to pass through the filter pores. This embodiment provides several advantages over the situation where the two particles are the same size. In the latter situation, aggregation typically occurs not only between individual particles to form pairs but also to form larger aggregates. Thus, the blocking of a single binding site does not automatically give rise to the release of a single ligand-bearing particle since it still may be held together in the aggregate by other bonds. The use of substantially larger binder particles, (containing a very small number of binding sites) in amounts in excess of the number of ligand coated particles reduces the number of large aggregates and increases the number of pairs of ligand-binder particles, thereby giving rise to the release of one particle for each blocking event.

In this invention, the amount of unaggregated particles which pass through the filter is proportional to the amount of ligand in the sample. Thus visual standards can be set showing the appearance, e.g., color, fluorescence or other variable, of a standard sample containing the upper limit of concentration. Then the filtrate from any given sample can simply be compared with the visual standard to determine whether the sample is or is not acceptable. Similarly, visual standards for minimum, maximum and intermediate concentration points within a desired range can be set up for sample evaluation.

While it is thus not normally necessary to employ additional instrumentalities in order to obtain quick accurate determinations of whether or not a ligand falls within a certain range it is certainly possible to do so. Moreover, the determination of the concentration of particles in the filtrate obtained from the present process is faster, more accurate and more reproducible than measurements taken in accordance with the previous approaches to particulate analysis referred to above. For one thing, previous approaches measured the entire melange of aggregated and unaggregated product with various techniques being utilized to distinguish relative amounts of the aggregated from the unaggregated particles in that melange. The present technique physically separates the aggregated from the non-aggregated particles, and thus permits the extremely accurate measurement of only the unaggregated particles.

A distinct advantage of the present invention is that it makes possible a direct or forward aggregation assay by measurement or analysis of the aggregated particles. This embodiment may be desirable when the ligand is multivalent and the binder is coated on a particle. This forward aggregation may be assayed by simply resuspending the aggregated particles after the non-aggregated particles have been removed into the filtrate. If desired, e.g. to enhance the analysis of those aggregated particles, they can then be disaggregated, e.g. by treatment with surface active agent or other chemical which will break the bonds between the binder and the ligand or between the particles and either the ligand or the binder. This technique differs substantially from the inhibition techniques previously known, such as turbidity measurements and others which deal with a system containing both aggregated and unaggregated particles, and permits substantially increased accuracy and ease of operation.

A major advantage of the present method is that the concentration of the particles in the filtrate can be measured instantaneously. Thus there is no need for flowing streams or the like for single particle counting or mathematical or electronic factoring to attempt to differentiate the single particles from the aggregates, which are primarily what is measured by turbidometric techniques.

Preferred particles to be used with the present invention are small, uniform diameter latex spheres, available in a variety of diameters, e.g., from Dow Chemical Company, in the United States, or from Rhone-Poulent in Europe. Other useful particles include carboxylated polystyrene, with or without reactive groups to facilitate reaction with the binder, such as amino groups, thio groups, carboxyl groups, or other reactive groups. Butadiene/styrene copolymers such as carboxylated styrene butadiene or acrylonitrile butadiene styrene, are also useful. Substituted and unsubstituted acrylic acid polymers, methacrylic acid polymers, and vinyl polymers are also suitable. Inorganic particles such as silicas, clay, carbons such as activated charcoal, and other materials on which the binder or ligand can be immobilized, can be used to advantage with the present invention. Other useful particulate materials will be readily apparent to the skilled in the art.

It is important that the particles all have approximately the same diameter, so that they will easily pass through about the same size filter aperture. Preferably the particles are about 0.01–100 $\mu$m in diameter, more preferably from about 0.01 to 10 $\mu$m. Most preferably the size of the particles is about 0.1 to 1.0 $\mu$m in diameter, and the diameters of the various particles do not vary from the nominal diameters by more than 30%, preferably not by more than 15%.

The particles are preferably utilized at relatively small concentrations in the fluids which carry them, in order to maximize the free movement of the particles in the system. Typically a suspension or mixture of from about 0.01% to about 10% by weight of the particles in a ligand such as a buffer solution are preferred.

As already indicated, the particles can be made opaque, or colored, or fluorescent by adding dyes, pigments or coatings.

If more specific information than that provided by normal visual observations is desired, a variety of additional techniques can be employed. As indicated, spectrophotometric techniques can provide exact concentrations with extreme precision, partially because of the fact that it is only the unaggregated particles (or aggregated particles in the case of the direct assay disclosed supra) which are being measured. Thus extremely simple, battery operated spectrophotometers, which would not be adequate with previous particulate assays, can be used to provide highly accurate results in accordance with the present invention. It may also be advantageous in some instances to attach a radioactive tag or a detectable enzyme or other material to some of the reactants or the particles used in the present invention. For example, one way the visual evaluation of the present test can be enhanced is to bind to some of the reactants or to the particles an enzyme or other compound which causes a color change on a particular substrate. Thus for example if the filtrate of the present invention causes that substrate to undergo a color change, it is clear that the filtrate contains the reactants or particles which bear that enzyme or compound.

The ligand and binding protein may be chemically bonded to the latex beads or other particles, but they need not be. Preferably the beads are coated with a substance to which the ligand or binding protein will adhere, such as bovine serum albumin, human serum albumin, etc. So long as the coating does not interfere with the binding between the ligand and the binding protein, this method can be used. This method is preferred when there is an risk that chemically binding either of the species would adversely affect the results. It is possible to adsorb or absorb the binder and/or the ligand directly onto the surface of the particle.

Where the ligand or binder has multiple functionality, i.e., it is "multivalent" or otherwise can bind to more than one antibody molecule, it is not necessary to attach that material to a particle in order to obtain effective aggregation and effective measurement. For example, an antibody, which has at least two binding sites, can be used to aggregate two particles having the appropriate antigen.

The invention will be further clarified with reference to the following example:

EXAMPLE 1

Attachment of Penicillin G Ligand to Latex Particles 0.1 moles of the sodium salt of penicillin G is dissolved in distilled water at 4° C. This is acidified with 1M HCl to precipitate the acid. The precipitate is extracted into dry chloroform at room temperature, and the chloroform is then evaporated to yield the dry penicillin G in acid form.

The resulting product is dissolved in dimethylformamide, to a concentration of 0.1 molar penicillin G. This material is put in activated form by admixture with 11% by volume of 1 molar N-hydroxysuccinimide in DMF and 11% by volume of 1 molar dicyclohexylcarbodiimide and incubated for 24 hours at room temperature. After filtration through a Whatman #1 filter, the filtrate is activated penicillin G.

To a solution of bovine serum albumin is added a sodium phosphate buffer containing 2% sodium borate (pH 8.2) is added 50 μml of the above solution of activated Penicillin G, with stirring, at 4° C. The stirring at that temperature is continued for 30 minutes. Thereafter the mixture is centrifuged at 10,000 G and the supernatant fluid is removed, and any precipitate is discarded. The resultant material is dialyzed against distilled water, with several changes of dialyzate to remove uncoupled penicillin.

The result is a solution containing a 5.5:1 mole ratio of conjugate of penicillin to bovine serum albumin containing 4.4 mg/ml of conjugated protein. The protein concentration may then be determined by the Lowry method, and the amount of penicillin G conjugation estimated, e.g., via spectral analysis.

Dow Chemical latex beads (#47781) having a diameter of 0.305 plus or minus 0.0084 microns (10% solids) is diluted to a 2% latex suspension in distilled water, and filtered through a Whatman #4 filter.

To one volume of the BSA/Penicillin conjugate described above, is added 9.6 mg/ml of solid BSA. This is mixed gently to dissolve the BSA. An equal volume of the 2% solution of the latex beads prepared as described above is added. This mixture is then incubated, first in a shaking water bath at 37° C. for two hours; then on a rotator at room temperature for one hour, and then overnight at 40° C. The resultant product is washed three times in an equal volume of 0.1M Phosphate Buffer (pH 6.5). The coated latex product is then resuspended at a level of 2% by weight in the 0.1M phosphate buffer.

The end result is a suspension containing 2% of latex beads coated with a 5.5 to one conjugate of penicillin G to BSA in a 0.1M solution of phosphate buffer containing 9.6 mg/ml of unconjugated BSA. The non-conjugated BSA is added to block further adsorbtion of proteins to the surface of the particles and also acts as a stabilizer to keep the coated particles from reacting or self-agglomerating. Any other non-reactive protein can be used for this purpose, and in some instances, the stabilizing protein in the solution may be dispensed with entirely.

EXAMPLE II

Preparation of Protein Binder

In this case the protein binder for the Penicillin G ligand is an antibody raised to penicillin G. Since antibodies have at least two binding sites, the present example demonstrates that it is unnecessary to utilize the double particle embodiment of the present invention, i.e., the embodiment where the ligand is placed on the surface of one particle and the binding protein is placed on another particle. Further, in order to demonstrate the effectiveness of the present test, a spectrophotometer is utilized to generate exact data regarding the concentration of ligand in the sample listed, whereas in practice a simple visual comparison will normally be enough to determine meeting or failure to meet concentration limitations.

A diluent for antiserum containing the binding compound (antibody for Penicillin G) is made up of one volume of 6% Dextran T500 (Pharmacia AG.) in normal saline, mixed with 2 volumes of saline buffered with 0.15M phosphate buffer (pH 7.2) and containing 4% sucrose and 0.1% sodium azide. The antiserum diluent is made up of 0.5% of the above mixture in normal mouse serum.

The anti-penicillin G antibody used is a monoclonal antibody made by the procedure described by Kohler et al., Nature, Vol. 256, p. 495 (1975); Kohler et al., Eur. J. Immunol. Vol. 16, p. 511 (1976), which are both incorporated herein by reference, in a Balb/C mouse. While monoclonal antibodies are naturally preferred, any antibody which is specific in its binding properties for the ligand of interest is suitable for use with the present invention.

EXAMPLE III

Inhibition Assay for Penicillin G

In order to determine the effectiveness of the present method, a series of concentrations of penicillin G in 0.07M phosphate buffer (pH 6.0) solution were tested. Six samples containing respectively 1 ng/ml, 10 ng/ml, 100 ng/ml, 1000 ng/ml and 10,000 ng/ml of penicillin G in 50 μl of 0.07M phosphate buffer (pH 6.0) were each mixed with 50 μl anti-penicillin G antibody in the antisera diluent of Example II in a 1 ml tube. After mixing, the reagents are drawn into a 2.0ml syringe fitted with a Leur lock connection. The needle is removed from the syringe, and the syringe is capped. The syringe plunger is moved back to bring the reagent into the barrel to ensure proper mixing. After incubation for five minutes the needle is reattached to the syringe and 0.07M phosphate buffer (pH 6.0) is slowly drawn up to a 2.0ml volume. The syringe is then gently inverted several times to evenly disperse the latex suspension.

After removing the needle, the syringe is attached to the inlet port of a 25mm diameter Swinnex filter adaptor (Millipore Corp.) containing an 0.4 micron Nuclepore polycarbonate filter, which filter has been pre-wetted with an 0.07M phosphate buffer (pH 6.0) containing 0.1 mg/ml of bovine serum albumin.

Once the syringe is secured to the Swinnex adaptor a gentle even pressure is applied to the barrel of the syringe. The filtrate is collected from the outlet port of the adaptor.

The filtrates are placed in glass cuvettes having a 1 cm light path and read in a spectrophotometer (Beckman DU) at a wavelength of 620nm. FIG. 1 shows the curve of % latex (% solids) in the filtrate versus the concentration of the ligand penicillin G in the sample tested.

EXAMPLE IV

Measurement of Penicillin G in Milk

One volume of a sample of raw milk is mixed with 0.5 volumes of a milk clarification solution containing 0.006% citric acid and 6.0% of disodium salt of ethylenediamine tetracetic acid in distilled water. After thorough mixing the solids are removed by filtration through a Whatman GF/A filter and a 0.22 μm filter (Millipore Corp). About 2.0 ml of milk yields roughly 800 μl of filtrate.

Figure 2:
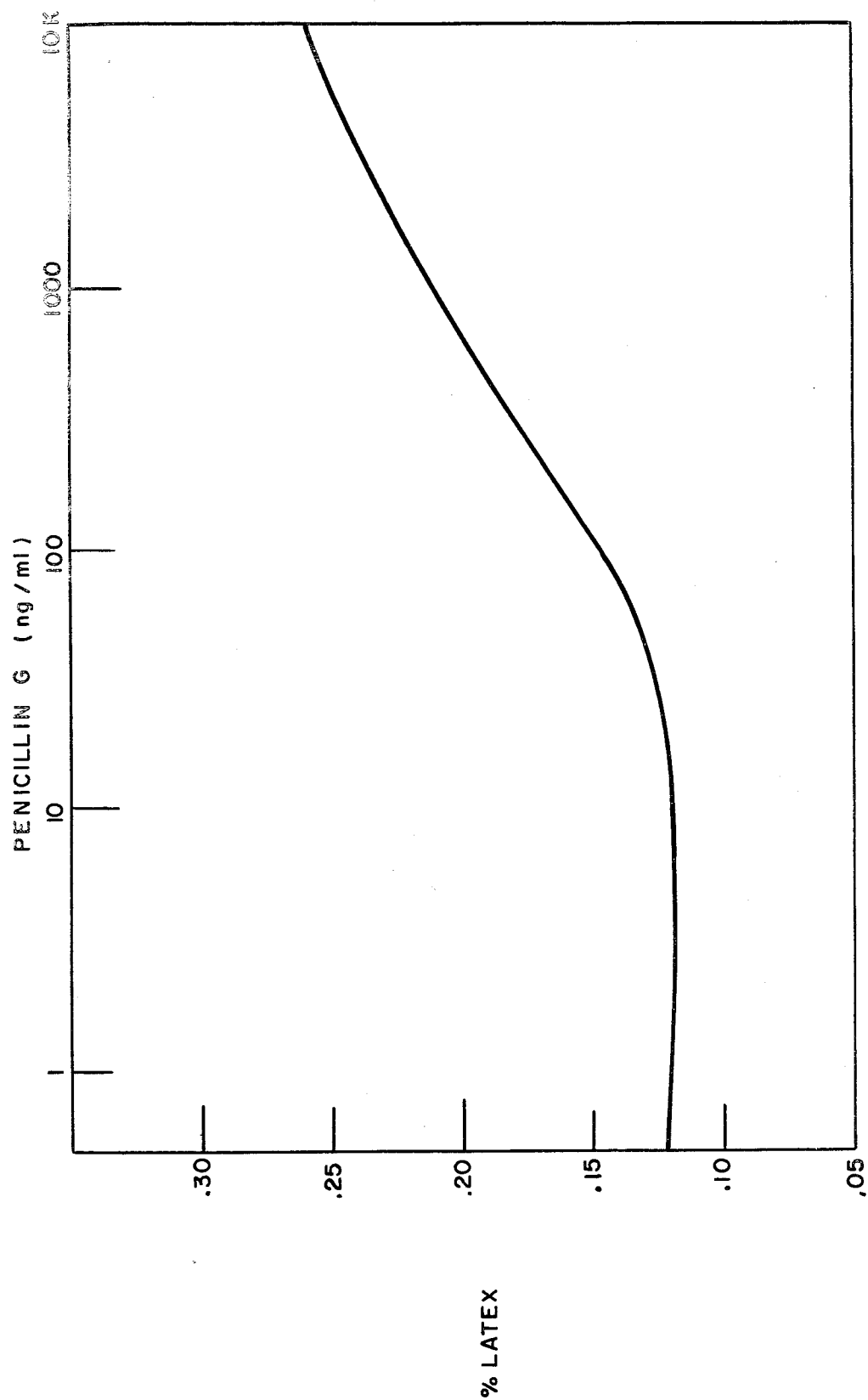
FIG. 2 is a graphical representation of a standard curve obtained by utilizing the present invention to measure various concentrations of penicillin G in milk.

50 μl portions of milk filtrate previously seeded with 1 ng/ml, 10 ng/ml, 100 ng/ml, 1000 ng/ml and 10,000 ng/ml of penicillin G are mixed with 50 μl of the coated latex of Example I and 50 μl of the anti-penicillin G solution of Example II, in the manner of Example III. The spectrophotometric results are depicted on FIG. 2. of the Drawings.

The specific embodiments described herein are meant to be exemplary only, and various modifications will be apparent to those skilled in the art. The claims below are intended to cover all such modifications.

I claim:

1. A method of analyzing a sample for a ligand, comprising incubating the sample with a binder, the binder being a nonparticulate material which specifically binds to the ligand and which binder has a plurality of binding sites for the ligand, and with particles of predetermined size bearing a predetermined amount of ligand on their outer surface, passing the mixture through a filter having apertures which are larger than the ligand-bearing particles but smaller than aggregates of the ligand-bearing particles, and analyzing at least one of the group of (a) the particles which pass through the filter and (b) the particles which do not pass through the filter.

2. The method of claim 1, wherein the incubation is carried out for a sufficient length of time to reach equilibrium in the reaction between the binder, and the ligand and the ligand-bearing particles.

3. The method of claim 1, wherein the ligand and is a protein, and the binder is an antibody to that protein.

4. The method of claim 1, wherein the particles which pass through the filter are analyzed.

5. The method of claim 4, wherein the analysis comprises determining the concentration of particles in the filtrate.

6. The method of claim 5, wherein the analysis of the filtrate is by comparison of the appearance of the filtrate with a visual standard corresponding to a known concentration of the ligand.

7. The method of claim 5, wherein the analysis of the filtrate is by meansuring the amount of polychromatic light or light of a predetermined wavelength which will pass through a standard volume of the filtrate.

8. The method of claim 4, wherein the particles are latex beads which are substantially uniform in size, having a diameter of from about 0.01 to 10 μm.

9. The method of claim 1, wherein the particles which do not pass through the filter are analyzed by resuspending the particles in liquid and determining the number of those particles relative to the total number of particles with which the sample was incubated.

10. A method of analyzing a sample for a ligand, comprising incubating the sample with binder particles, which binder particles comprise particles of predetermined size having a material on their outer surface which specifically bind to the ligand, and with ligand-bearing particales of predetermined size bearing a predetermined amount of the ligand on their outer surface, passing the mixture through a filter which has apertures which are large enough to pass individual particles but smaller than aggregates of the binder particles and the ligand-bearing particles, either the ligand-bearing particles or the binder particles (1) being larger than the apertures and larger than the other particles, (2) bearing a small number of binding sites, and (3) being in excess of the other particles, and analyzing at least one of the group of (a) the particles which pass through the filter and (b) the particles which do not pass through the filter.

11. The method of claim 10, wherein the incubation is carried out for a sufficient length of time to reach equilibrium in the reaction between the binder particles, the ligand and the ligand-bearing particles.

12. The method of claim 10, wherein the particles that pass through the filter are analyzed.

13. The method of claim 12, wherein the binder particles are larger than the filter apertures.

14. The method of claim 12, wherein the ligand-bearing particles are larger than the filter aperture.

15. An assay kit for analysis of a ligand, comprising binder particles which comprise particles of predetermined size bearing on their outside surface a binder material which specifically binds to the ligand, competitive binding particles comprising particles of a predetermined size bearing a predetermined amount of ligand on their outer surface, and a filter having apertures which are larger than the competitive binding particles but smaller than aggregates of competitive binder particles with binder particles, either the ligand-bearing particles or the binder particles (1) being larger than the apertures and larger than the other particles, (2) bearing a small number of binding sites, and (3) being in excess of the other particles.

16. The method of claim 9, wherein the particles which do not pass through the filter are disaggregated prior to determination of the number of particles.

17. The method of claim 10, wherein the amounts of binder and ligand borne by the particles, and the number of particles are such that, in the absence of inhibition, each of the binder particles binds with one or more of the ligand bearing particles.

18. A method of analyzing a sample for a ligand, comprising incubating the sample with a binder and with a predetermined amount of ligand, the binder being a non-particulate material which specifically binds to the ligand at a plurality of binding sites, the binder being borne by particles of predetermined size on their outer surface, passing the mixture through a filter having apertures which are larger than the binder-bearing particles but smaller than aggregation of the binder-bearing particles, and analyzing at least one of the group of (a) the particles which pass through the filter and (b) the particles which do not pass through the filter.

19. The method of claim 18, wherein the incubation is carried out for a sufficient length of time to reach equilibrium in the reaction between the ligand and the binder-bearing particles.

20. The method of claim 18, wherein the ligand is a protein, and the binder is an antibody to that protein.

21. The method of claim 18, wherein the analysis comprises determining the concentration of particles in the filtrate.

22. The method of claim 21, wherein the analysis of the filtrate is by comparison of the appearance of the filtrate with a visual standard corresponding to a known concentration of the ligand.

23. The method of claim 18, wherein the particles which do not pass through the filter are analyzed by resuspending the particles in liquid and determining the number of those particles relative to the total number of particles with which the sample was incubated.

* * * * *